(12) United States Patent
Motegi

(10) Patent No.: US 10,478,478 B2
(45) Date of Patent: Nov. 19, 2019

(54) TREATMENT OF RAYNAUD'S PHENOMENON USING BOTULINUM TOXIN TYPE B

(71) Applicant: NATIONAL UNIVERSITY CORPORATION GUNMA UNIVERSITY, Gunma (JP)

(72) Inventor: Sei-ichiro Motegi, Gunma (JP)

(73) Assignee: NATIONAL UNIVERSITY CORPORATION GUNMA UNIVERSITY, Gunma (JP)

( * ) Notice: Subject to any disclaimer, the term of this patent is extended or adjusted under 35 U.S.C. 154(b) by 0 days.

(21) Appl. No.: 15/941,089

(22) Filed: Mar. 30, 2018

(65) Prior Publication Data

US 2018/0280484 A1    Oct. 4, 2018

(30) Foreign Application Priority Data

Mar. 31, 2017   (JP) ................. 2017-072001

(51) Int. Cl.
*A61K 38/48* (2006.01)
*A61K 9/00* (2006.01)
*A61P 9/00* (2006.01)

(52) U.S. Cl.
CPC ........ *A61K 38/4893* (2013.01); *A61K 9/0019* (2013.01); *A61P 9/00* (2018.01)

(58) Field of Classification Search
None
See application file for complete search history.

(56) References Cited

U.S. PATENT DOCUMENTS

| | | | | |
|---|---|---|---|---|
| 6,974,579 B2* | 12/2005 | Brin | ............ | A61K 38/4893 424/184.1 |
| 2005/0152923 A1 | 7/2005 | Brin et al. | | |
| 2006/0057166 A1* | 3/2006 | Brin | ............ | A61K 38/4893 424/239.1 |
| 2011/0212157 A1* | 9/2011 | Edelson | ........... | A61K 9/1075 424/443 |
| 2012/0321579 A1* | 12/2012 | Edelson | ........ | A61K 45/06 424/66 |
| 2015/0239932 A1* | 8/2015 | Cerami | ........... | C07K 14/505 514/15.4 |
| 2015/0313536 A1* | 11/2015 | Edelson | ........ | A61K 38/4893 424/130.1 |
| 2016/0213757 A1* | 7/2016 | Edelson | .......... | A61K 9/1075 |
| 2018/0280484 A1* | 10/2018 | Motegi | .......... | A61K 38/4893 |

FOREIGN PATENT DOCUMENTS

| | | |
|---|---|---|
| JP | 2007-517890 | 7/2007 |
| WO | WO-2009158687 A1 * | 12/2009 |
| WO | WO-2012103037 A1 * | 8/2012 |
| WO | WO-2012103040 A1 * | 8/2012 |
| WO | WO-2015168562 A1 * | 11/2015 |

OTHER PUBLICATIONS

Clemens et al, Plast. Reconstr. Surg. 123: 64, 2009. (Year: 2009).*
Grando et al, British Journal of Dermatology (2018) 178, pp. 1011-1019 (Year: 2018).*
Jenkins et al, J Am Acad Dermatol Nov. 2013. vol. 69, No. 5, pp. 834-835 (Year: 2013).*
Iorio et al, Semin Arthritis Rheum., 2012, 41:599-603 (Year: 2012).*
Motegi et al, Journal of Dermatology (2016), 43(1), 56-62. abstract only (Year: 2016).*
Motegi et al, Journal of Dermatological Science, (May 2017) vol. 86, No. 2, pp. e27. Abstract Number: P04-04[C06-1]. Meeting Info: 41st Annual Meeting of the Japanese Society for Investigative Dermatology, JSID 2016. Sendai, Japan. 09 (Abstract Only) (Year: 2016).*
Motegi et al. JID, 2017, S197, abstract #030. (Abstract Only) (Year: 2017).*
Motegi et al Acta Derm Venereol 2017; 97: 843-850. Epub ahead of print Mar. 30, 2017 (Year: 2017).*
Neumeister et al, Plast. Reconstr. Surg. 124: 191-200, 2009 (Year: 2009).*
Patil et al, Curr Pain Headache Rep (2016) 20: 15, 8 pages. published online:Feb. 15, 2016 (Year: 2016).*
Segreto et al, Ann Plast Surg Sep. 2016;77/3: 318-323 (Year: 2016).*
Sekiguchi et al, Journal of Dermatological Science 90 (2018) 144-153 (Year: 2018).*
Uchiyama et al, J. Investigative Dermatology, (Sep. 2015) vol. 135, Supp. SUPPL. 2, pp. S30. Abstract No. 171. Meeting Info: 45th Annual Meeting of the European Society for Dermatological Research. Rotterdam, Netherlands. Sep. 9, 2015-Sep. 12, 2015 (Year: 2015).*
Al-Ghamdi et al, Journal of Dermatology & Dermatologic Surgery 19 (2015) 1-8 . . . available online: Sep. 18, 2014 (Year: 2015).*
Levien, TL. Vascular Health and Risk Management 2010:6 167-177. publication date Mar. 2010 (Year: 2010).*
Neumeister, MW. 2010. Botulinum toxin type A in the treatment of Raynaud's phenomenon. J. Hand surg. Am. 35/12:2085-2092 (abstract only) (Year: 2010).*
Sycha et al, European J. Clinical Investigation. 2004. 34(4):312-313. (Year: 2004).*
Lauren Smith et al., "Botulinum Toxin-A for the Treatment of Raynaud Syndrome", Arch Dermatol, 2012, vol. 148, No. 4, pp. 426-428.
Michael W. Neumeister, MD, "Botulinum Toxin Type A in the Treatment of Raynaud's Phenomenon", The Journal of Hand Surgery, 2010, vol. 35A, pp. 2085-2092.
Michael W. Neumeister et al., "Botox Therapy for Ischemic Digits", Plastic and Reconstructive Surgery, 2009, vol. 124, pp. 191-200.
Alero Fregene et al., "Botulinum Toxin Type A: A Treatment Option for Digital Ischemia in Patients with Raynaud's Phenomenon", The Journal of Hand Surgery, 2009, 34A, pp. 446-452.

(Continued)

*Primary Examiner* — Nita M. Minnifield
(74) *Attorney, Agent, or Firm* — Wenderoth, Lind & Ponack, L.L.P.

(57) ABSTRACT

An effective amount of botulinum toxin type B is administered to a subject in need thereof for treating Raynaud's phenomenon. Botulinum toxin type B may be in a form of an injection, and may be locally administered to a disease affected site, in a dose of 200 to 400 units per disease affected site.

2 Claims, 3 Drawing Sheets

(56) References Cited

OTHER PUBLICATIONS

Allen L. Van Beek, M.D., et al. "Management of Vasospastic Disorders with Botulinum Toxin A", Plastic and Reconstructive Surgery, 2007, vol. 119, pp. 217-226.
T. Sycha et al., "Botulinum toxin in the treatment of Raynaud's phenomenon: a pilot study", European Journal of Clinical Investigation, 2004, vol. 34, No. 4, pp. 312-313.
Sei-ichiro Motegi et al., "Beneficial effect of botulinum toxin A on Raynaud's phenomenon in Japanese patients with systemic sclerosis: A prospective, case series study", Journal of Dermatology, 2016, vol. 43, pp. 56-62.
Anna Rita Bentivoglio et al., "Clinical differences between botulinum neurotoxin type A and B", Toxicon, 2015, vol. 107, Part A, pp. 77-84.
Office Action dated Aug. 28, 2018 issued in corresponding Japanese patent application No. 2017-072001, with machine translation.
Patil, S. et al., "Botulinum Toxin: Pharmacology and Therapeutic Roles in Pain States", Curr. Pain Headache Rep., 2016, 20:15, 8 pages.

\* cited by examiner

TREATMENT OF RAYNAUD'S PHENOMENON USING BOTULINUM TOXIN TYPE B

TECHNICAL FIELD

The present invention relates to a pharmaceutical, more specifically, a method of treatment of Raynaud's phenomenon using botulinum toxin type B.

BACKGROUND ART

Raynaud's phenomenon is a phenomenon in which the color tone of fingers suddenly changes, as a result of arteriolar spasm in fingers, transient ischemia in the distal portion, and subsequent reperfusion. This phenomenon is induced by cold stimulation or psychological stress. The arteriolar ischemia-reperfusion in fingers causes triphasic changes in the color into white (ischemia), purple (cyanosis), and red (reperfusion). Since the phenomenon accompanies pain and numbness for a long period, the daily life of the patient is seriously affected, leading to a remarkable decrease in QOL. Due to decreased peripheral blood flow, circulatory disturbance easily occurs, and even a mild injury is likely to cause an ulcer. Fingertip ulcers due to Raynaud's phenomenon are often intractable. If bacterial infection occurs, the ulcer may be enlarged, and osteomyelitis and arthritis may occur, resulting in amputation of digits in some cases. Since bacterial infection of a wound may cause sepsis to affect survival prognosis, appropriate treatment at an early stage is important.

Common examples of current pharmacotherapy for Raynaud's phenomenon include use of a drug having a vasodilator action or antiplatelet action such as a vitamin E preparation (tocopherol nicotinate etc.), calcium antagonist (Nifedipine etc.), prostaglandin preparation (oral drug: limaprost or beraprost; injection: alprostadil), scrotonin antagonist (sarpogrelate hydrochloride), or platelet aggregation inhibitor (cilostazol or dipyridamole); infusion of an anticoagulant argatroban; and use of an endothelin receptor antagonist (bosentan). However, these oral drugs and infusions are poorly effective.

In recent years, there were some reports on remarkable amelioration of symptoms of Raynaud's phenomenon by local injection of botulinum toxin type A (Non-patent Documents 1 to 6). Botulinum toxin is a neurotoxin produced from *Clostridium botulinum*. Botulinum toxin is incorporated from nerve endings by endocytosis, and cleaves a specific site of a protein complex which is directly involved in fusion of synaptic vesicles to the presynaptic membrane (fusion complex). This causes inhibition of Ca-dependent acetylcholine release from synaptic vesicles. As a result, neuromuscular transmission is inhibited and muscle paralysis is induced. Depending on the type of the toxin, the protein cleaved varies. Botulinum toxin type B specifically cleaves VAMP (vesicle-associated membrane protein: synaptobrevin: one of the synaptic vesicle membrane proteins), and botulinum toxin type A specifically cleaves SNAP-25 (synaptosome-associated protein of molecular weight 25,000 dalton: one of the membrane-bound proteins present in the presynaptic membrane), to suppress acetylcholine release from the peripheral cholinergic nerve endings, causing inhibition of neuromuscular transmission, resulting in muscle paralysis. Thus, although these toxin types have different mechanisms of suppression of acetylcholine release, they are considered to have the same inhibitory action on neuromuscular transmission.

In Raynaud's phenomenon, suppression of arteriolar spasm (transient contraction) in digits and improvement of peripheral circulation can be expected by allowing botulinum toxin to block signal transduction to vascular smooth muscle. Further, amelioration of pain and numbness in Raynaud's phenomenon can be expected by allowing botulinum toxin to suppress neurotransmitters (for example, substance P) that cause the pain and the numbness.

The inventor of the present invention carried out an investigator-initiated independent study in which botulinum toxin type A was injected into the base of a finger in each of 10 patients with Raynaud's phenomenon. One finger exhibiting Raynaud's phenomenon was selected, and 10 units of botulinum toxin type A was subcutaneously injected at each of the left and right on the base of the finger (20 units in total). Four weeks after the administration, severity (frequency, color, duration, and the like) of Raynaud's symptoms according to the Raynaud's score, as well as pain and numbness (VAS), were significantly lower than those before the administration, and the effect could be continuously observed for 16 weeks. The degree of recovery of the skin temperature during the 20-minute period immediately after application of cold water load was significantly higher at Week 4 compared to that before the administration. Total epithelialization of fingertip ulcers (5 cases) was achieved by Week 12. In all cases, no side effect such as muscle weakness or pain was found. By this independent study, safety and effectiveness of local injection of 10 units of botulinum toxin type A could be confirmed (Non-patent Document 7).

Botulinum toxin type B is known, for example, to be less expensive than type A by about 40%, to show the effect quickly, and to be highly effective for pain. However, there has been no report on a test of a therapeutic effect of botulinum toxin type B on Raynaud's phenomenon. Although Patent Document 1 discloses utilization of botulinum toxin for Raynaud's phenomenon, it was mainly utilization of type A, and the document does not show actual clinical data.

It has been thought that an almost equivalent effect can be produced when botulinum toxin type B is used in an amount (units) corresponding to the ratio A:B=1:20 to 40 (Non-patent Document 8), but the concentration at which a therapeutic effect is produced against Raynaud's phenomenon is not clear.

PRIOR ART DOCUMENTS

[Patent Document 1] JP2007-517890A
[Non-patent Document 1] Arch Dermatol. 2012; 148: 426-428.
[Non-patent Document 2] J Hand Surg. 2010; 35A: 2085-2092.
[Non-patent Document 3] Plast Reconstr Surg. 2009; 124: 191-201.
[Non-patent Document 4] J Hand Surg. 2009; 34A: 446-452
[Non-patent Document 5] Plast Reconstr Surg. 2007; 119: 217-226.
[Non-patent Document 6] Eur J Clin Invest. 2004; 34: 312-313.
[Non-patent Document 7] J Dermatol. 2016; 43(1): 56-62.
[Non-patent Document 8] Toxicon. 2015: 107(Pt A): 77-84.

SUMMARY OF THE INVENTION

An object of the present invention is to provide a therapeutic agent for Raynaud's phenomenon, which therapeutic agent is inexpensive and has excellent efficacy.

As a result of intensive study for solving the above problem, the present inventors discovered that botulinum toxin type B shows safety and effectiveness in treatment of Raynaud's phenomenon, and identified the volume and the concentration of botulinum toxin type B at which it exerts a therapeutic effect on Raynaud's phenomenon. In one aspect, a method of treating Raynaud's phenomenon comprising administering an effective amount of botulinum toxin type B to a subject in need thereof is provided.

Raynaud's phenomenon is a phenomenon in which transient spasm of peripheral arteries occurs to cause changes in the color of fingers. It accompanies pain and numbness for a long period, seriously affecting the daily life of the patient, leading to a remarkable decrease in QOL. In most cases, use of an approved therapeutic agent fails to suppress occurrence of Raynaud's phenomenon, often allowing exacerbation of the symptoms. Such absence of an established effective therapeutic method has been a problem. By application of botulinum toxin type B local injection therapy to such Raynaud's phenomenon whose amelioration cannot be achieved by existing therapeutic methods, symptoms of Raynaud's phenomenon such as numbness, pain, and cold sense can be expected to be ameliorated. Further, the therapy enables prevention and treatment of various complications caused by Raynaud's phenomenon (finger ulcer, bacterial infection, gangrene, and the like). The therapy also leads to shortening of the treatment period, reduction of the burden on the patient, and saving of the medical cost.

EMBODIMENTS FOR CARRYING OUT THE INVENTION

Figure 1:
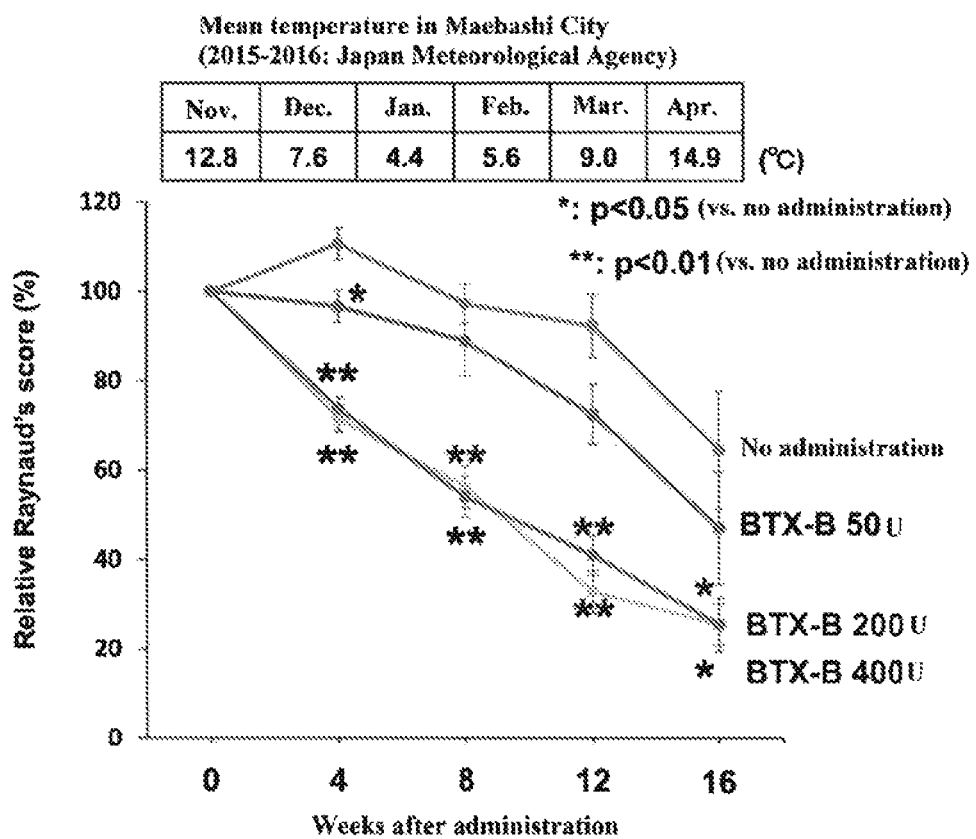
FIG. 1 is a graph illustrating changes in the Raynaud's score due to administration of botulinum toxin type B.

In one aspect, a method of treating Raynaud's phenomenon comprising administering an effective amount of botulinum toxin type B to a subject in need thereof is provided.

Raynaud's phenomenon can be clinically diagnosed based on, for example, color changes in fingers, and the severity of the phenomenon can be diagnosed based on the Raynaud's score and the like.

Botulinum toxin is a collective term encompassing toxins produced by an anaerobic bacterium *Clostridium botulinum*. At present, seven immunologically different neurotoxin serotypes (A, B, C, D, E, F, and G) have been found in botulinum toxin.

In the present invention, botulinum toxin type B, which is produced by *Clostridium botulinum* and has a molecular weight of about 150 kDa, may be used, but a complex of a non-toxin protein and botulinum toxin type B protein (molecular weight, about 500 kDa) may also be used.

The botulinum toxin type B may be obtained by purification from *Clostridium botulinum*, or may be produced by genetic recombination. The botulinum toxin type B may also be a partial protein or a mutant as long as it has a therapeutic effect on Raynaud's phenomenon.

As the botulinum toxin type B, a commercially available preparation may be used. For example, NerBloc (trade name; Eisai Co., Ltd.) may be used.

A pharmaceutical composition for treatment of Raynaud's phenomenon of the present invention may be formulated into an arbitrary dosage form. Examples of the dosage form include liquids, suspensions, and injection solutions. Injection solutions are preferred. For the pharmaceutical composition, pharmacologically acceptable carriers such as diluents, stabilizers, and surfactants may be used.

The pharmaceutical composition for treatment of Raynaud's phenomenon to be used in the method of the present invention may further contain an effective component of another therapeutic agent for Raynaud's phenomenon. Examples of such a component include drugs having a vasodilator action or antiplatelet action such as vitamin E, calcium antagonists, prostaglandin, serotonin antagonists, and platelet aggregation inhibitors; anticoagulants; and endothelin receptor antagonists.

The concentration of the effective component (botulinum toxin type B) in the pharmaceutical composition for treatment of Raynaud's phenomenon to be used in the method of the present invention is not limited, and may be, for example, 0.1 to 100% (w/w), 0.5 to 50% (w/w), or 1 to 25% (w/w).

The mode of administration is not limited. For example, the composition is preferably locally administered by injection or the like to a disease affected area including a finger or the like.

The dose of the botulinum toxin type B to be used in the method of the present invention is not limited as long as Raynaud's phenomenon can be treated. It may be appropriately set depending on conditions such as the age, sex, and body weight of the patient, and the severity. The dose of the effective component per site is preferably 200 to 400 units. In this case, 1 unit corresponds to the 50% lethal dose in cases of intraperitoneal administration of botulinum toxin to mice with body weights of 18 to 22 g. The pharmaceutical composition for treatment of Raynaud's phenomenon may be administered once daily, or dividedly several times per day. Alternatively, the pharmaceutical composition for treatment of Raynaud's phenomenon may be administered once per several days or several weeks. The dose for each time of administration may be either constant or variable in terms of the dose of the effective component.

Examples

The present invention is described below more concretely by way of Examples. However, the modes of the present invention are not limited to the following.

The inventor carried out a study in which botulinum toxin type B was injected to the bases of fingers of 45 patients with Raynaud's phenomenon (approved by IRB in Gunma University Hospital (2015, 11, 1); UMIN trial ID: UMIN000019985). The hand more strongly showing Raynaud's phenomenon was selected, and, at the sites between the fingers and at the external sides of the metacarpophalangeal joints of the first and fifth fingers (a total of six sites), a total of 250 units (50 units per site; half amount at both ends), 1000 units (200 units per site; half amount at both ends), or 2000 units (400 units per site; half amount at both ends) of botulinum toxin type B was subcutaneously injected. Comparison with an untreated group was also carried out. The patients were randomly assigned to the above four groups, and the study was carried out in a blinded manner.

Figure 2:
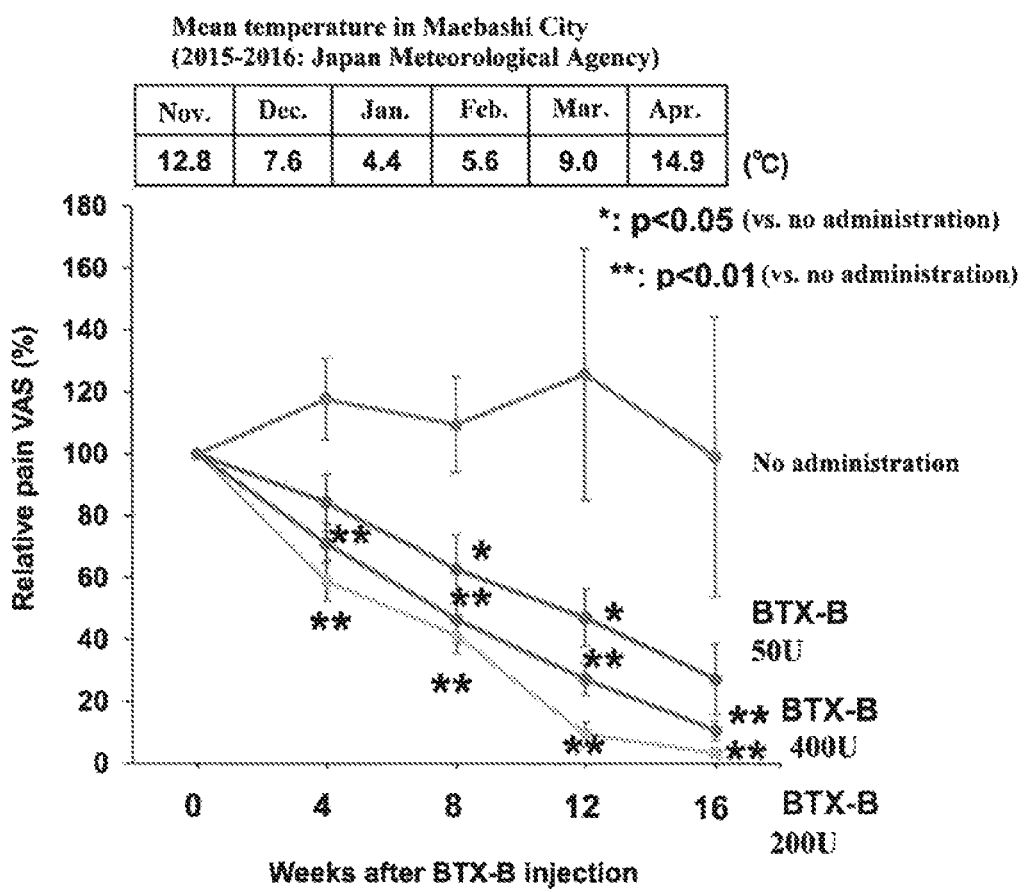
FIG. 2 is a graph illustrating changes in VAS (Visual Analogue Scale) due to administration of botulinum toxin type B.

In terms of the severity of Raynaud's symptoms (frequency, color, duration, and the like) according to the Raynaud's score (Table 1, FIG. 1) and VAS for evaluation of pain and numbness (Table 2, FIG. 2), continuous and significant decreases during the period from Week 4 to Week 16 after the administration were found in the groups with administration of not less than 200 units, relative to the non-administration group. However, regarding comparison with the 50-unit group, while significant differences in the Raynaud's score were found during the observation period in the groups with administration of not less than 200 units, no significant difference in VAS was found between the 50-unit group and the groups with administration of not less than 200 units.

TABLE 1

Raynaud's score - comparison with the value observed before the administration (%)

| | Day of administration | Week 4 | Week 8 | Week 12 | Week 16 |
|---|---|---|---|---|---|
| No administration | — | 110.6 ± 10.1 | 97.2 ± 12.3 | 92.3 ± 20.0 | 64.5 ± 37.5 |
| 50U | — | 96.6 ± 10.7 | 88.9 ± 23.6 | 72.5 ± 20.0 | 61.6 ± 32.1 |
| 200U | — | 71.4 ± 9.1 | 56.2 ± 15.0 | 32.8 ± 15.2 | 28.8 ± 14.9 |
| 400U | — | 73.8 ± 10.7 | 54.0 ± 20.0 | 41.0 ± 18.8 | 30.5 ± 15.5 |

TABLE 2

VAS - comparison with the value observed before the administration (%)

| | Day of administration | Week 4 | Week 8 | Week 12 | Week 16 |
|---|---|---|---|---|---|
| No administration | — | 117.6 ± 37.1 | 109.5 ± 43.4 | 125.7 ± 115.1 | 99.1 ± 128.1 |
| 50U | — | 84.3 ± 27.1 | 62.8 ± 33.9 | 47.1 ± 27.6 | 34.6 ± 35.0 |
| 200U | — | 58.9 ± 21.0 | 41.2 ± 17.9 | 9.4 ± 12.6 | 3.4 ± 5.5 |
| 400U | — | 71.0 ± 27.0 | 46.5 ± 33.0 | 27.2 ± 22.2 | 16.3 ± 17.9 |

Figure 3:
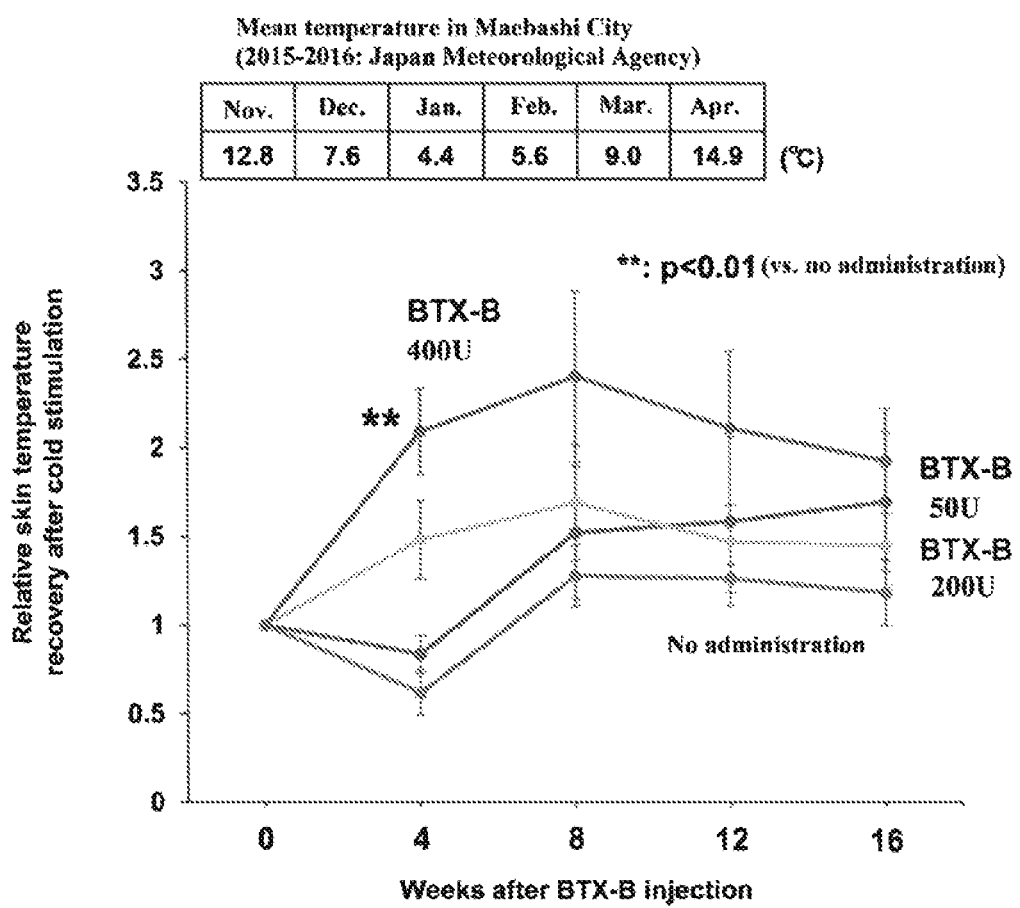
FIG. 3 is a graph illustrating changes, due to administration of botulinum toxin type B, in the degree of recovery of the skin temperature after application of cold water load.

In a cold water load test, the degree of recovery of the skin temperature during the 10-minute period immediately after application of cold water load was significantly higher in the 400-unit group than in the non-administration group or 50-unit group at Week 4 after the administration. At Week 8 and later, no significant difference was found among the groups in the cold water load test, but a tendency of dose-dependent amelioration was found (Table 3, FIG. 3).

TABLE 3

Degree of recovery of the skin temperature after application of cold water load - comparison with the value observed before the administration (° C.)

| | Day of administration | Week 4 | Week 8 | Week 12 | Week 16 |
|---|---|---|---|---|---|
| No administration | — | 0.62 ± 0.13 | 1.28 ± 0.17 | 1.26 ± 0.08 | 1.18 ± 0.18 |
| 50U | — | 0.84 ± 0.11 | 1.52 ± 0.37 | 1.58 ± 0.48 | 1.69 ± 0.39 |
| 200U | — | 1.48 ± 0.22 | 1.69 ± 0.32 | 1.47 ± 0.20 | 1.45 ± 0.26 |
| 400U | — | 2.09 ± 0.24 | 2.40 ± 0.48 | 2.11 ± 0.44 | 1.92 ± 0.30 |

Earlier epithelialization of fingertip ulcers was found in the 200-unit group (the group with administration of 200 units per site, a total of 1000 units) and the 400-unit group (the group with administration of 400 units per site, a total of 2000 units), compared to the non-administration group or the 50-unit group (the group with administration of 50 units per site, a total of 250 units). In the 200-unit group and the 400-unit group, formation of a new ulcer was not found until Week 16 after the administration, and the ulcer amelioration rate was 100% (Tables 4 to 6).

TABLE 4

Changes in the total number of ulcers

| | Day of administration | Week 4 | Week 8 | Week 12 | Week 16 |
|---|---|---|---|---|---|
| No administration (n = 8) | 3 | 7 | 5 | 5 | 4 |
| 50U (n = 9) | 5 | 3 | 3 | 4 | 3 |
| 200U (n = 10) | 3 | 0 | 0 | 0 | 0 |
| 400U (n = 18) | 13 | 3 | 1 | 1 | 0 |

TABLE 5

Number of newly formed ulcers

| | Day of administration | Week 4 | Week 8 | Week 12 | Week 16 |
|---|---|---|---|---|---|
| No administration (n = 8) | — | 4 | 1 | 1 | 1 |
| 50U (n = 9) | — | 0 | 0 | 2 | 0 |
| 200U (n = 10) | — | 0 | 0 | 0 | 0 |
| 400U (n = 18) | — | 0 | 0 | 0 | 0 |

TABLE 6

Ulcer amelioration rate (%)

| | Day of administration | Week 4 | Week 8 | Week 12 | Week 16 |
|---|---|---|---|---|---|
| No administration (n = 3) | — | 0 (0/3) | 0 (0/3) | 0 (0/3) | 0 (0/3) |

TABLE 6-continued

| | Ulcer amelioration rate (%) | | | | |
|---|---|---|---|---|---|
| | Day of administration | Week 4 | Week 8 | Week 12 | Week 16 |
| 50U (n = 3) | — | 33.3 (1/3) | 33.3 (1/3) | 66.7 (2/3) | 66.7 (2/3) |
| 200U (n = 3) | — | 100 (3/3) | 100 (3/3) | 100 (3/3) | 100 (3/3) |
| 400U (n = 6) | — | 50 (3/6) | 83.3 (5/6) | 83.3 (5/6) | 100 (6/6) |

Regarding the safety, only one case of finger muscle weakness was found in the 400-unit group. The muscle weakness appeared on Day 5 after the administration, but improved three weeks later (Table 7).

TABLE 7

| State of occurrence of adverse events (number of patients (event that occurred)) | | | | | |
|---|---|---|---|---|---|
| | Day of administration | Week 4 | Week 8 | Week 12 | Week 16 |
| No administration | — | — | — | — | — |
| 50U | — | — | — | — | — |
| 200U | — | — | — | — | — |
| 400U | — | 1 (Muscle weekness) | — | — | — |

These results suggest effectiveness and safety of botulinum toxin type B for Raynaud's phenomenon, and it is therefore expected that botulinum toxin type B local injection may be established as a more effective therapeutic method for Raynaud's phenomenon. Another advantage of the botulinum toxin treatment is that the effectiveness can be expected for several months even with single injection.

Bosentan, which is used for treatment of finger skin ulcers in scleroderma, has not been shown to have a therapeutic effect on skin ulcers in clinical trials, and it is indicated for prevention of new occurrence of ulcers. Since adverse events caused by liver dysfunction appear in about 50% of patients who received bosentan (Hamaguchi Y, Sumida T, Kawaguchi Y, Ihn H. Tanaka S, Asano Y, Motegi S, Kuwana M, Endo H, Takehamr K. Safety and tolerability of bosentan for digital ulcers in Japanese patients with systemic sclerosis: Prospective, multicenter, open-label study. J Dermatol 2017, 44(1), 13-17.), its administration needs to be carefully carried out, and it cannot be used for patients with liver dysfunction. In contrast, botulinum toxin type B has not shown such serious adverse events in the past clinical trials.

While the invention has been described in detail with reference to exemplary embodiments thereof, it will be apparent to one skilled in the art that various changes can be made, and equivalents employed, without departing from the scope of the invention. Each of the aforementioned documents as well as JP2017-072001 is incorporated by reference herein in its entirety.

What is claimed is:

1. A method of treating Raynaud's phenomenon, comprising administering a therapeutically effective amount of botulinum toxin type B to a subject in need thereof, wherein said botulinum toxin type B is injected to sites between fingers and at the external sides of metacarpophalangeal joints of the first and fifth fingers of the subject.

2. The method according to claim 1, wherein said botulinum toxin type B is injected to the subject at a dose of 200 to 400 units per one injection.

\* \* \* \* \*